(12) United States Patent
Rausch

(10) Patent No.: US 6,784,339 B1
(45) Date of Patent: Aug. 31, 2004

(54) TRANSGENIC PLANTS AND PLANT CELLS COMPRISING A REDUCED EXPRESSION OF INVERTASE INHIBITORS

(76) Inventor: Thomas Rausch, Im Neuenheimer Feld 360, D-69120, Heidelberg (DE)

(*) Notice: Subject to any disclaimer, the term of this patent is extended or adjusted under 35 U.S.C. 154(b) by 0 days.

(21) Appl. No.: 09/762,782
(22) PCT Filed: Aug. 11, 1999
(86) PCT No.: PCT/EP99/05890
   § 371 (c)(1),
   (2), (4) Date: Mar. 30, 2001
(87) PCT Pub. No.: WO00/09719
   PCT Pub. Date: Feb. 24, 2000

(30) Foreign Application Priority Data

Aug. 12, 1998 (DE) .......................................... 198 36 405

(51) Int. Cl.[7] .............................. A01H 5/00; A01H 5/10; C12N 15/29; C12N 15/82; C12N 15/84
(52) U.S. Cl. ........................ 800/286; 800/278; 800/292; 800/293; 800/294; 800/298; 435/419; 435/320.1; 536/23.6
(58) Field of Search ................................ 800/278, 298, 800/286, 288, 293, 294, 292, 306, 312, 320.1, 320.3, 320.7, 328, 320; 435/419, 430, 412, 415, 416, 465, 470, 469, 320.1; 536/23.6

(56) References Cited

U.S. PATENT DOCUMENTS 6,384,300 B1 * 5/2002 Rausch ....................... 800/284

FOREIGN PATENT DOCUMENTS

| DE | WO 98/04772 A1 | * | 2/1998 | ........... C12N/15/82 |
| WO | 97/07221 | | 2/1997 | |
| WO | 98/04722 | | 2/1998 | |

OTHER PUBLICATIONS

Broun, P. et al., Jul. 31, 2001, PNAS, vol. 98, No. 16, pp. 8925–8927.*
Broun, P. et al., Nov. 13, 1998, Science vol. 282, pp. 1315–1317.*
Elomaa, P. et al. Molecular Breeding 1996, 2: pp. 41–50.*
Bussis, D. et al., Planta 1997, 202: pp. 126–136.*
Gordon–Kamm et al. The Plant Cell, Jul. 1990, vol. 2, pp. 603–618.*
S. Greiner, et al., "Cloning of A Tobacco Apoplasmic Invertase Inhibitor", *Plant Physiology*, (1998) 116: 733–742.
S. Krausgrill, et al., "In Transformed Tobacco Cells The Apoplasmic Invertase Inhibitor Operates As A Regulatory Switch of Cell Wall Invertase", *The Plant Journal*, (1998) 13(2): 275–280.
S. Krausgrill, et al., "Regulation of Cell Wall Invertase by A Proteinaceous Inhibitor", *Journal of Experimental Botany*, Great Britain, Oxford University Press, vol. 47, pp. 1193–1198.
A. Sander, et al., "Sucrose Protects Cell Wall Invertase But Not Vacuolar Invertase Against Proteinaceous Inhibitors", *FEBS Letters*, NL, Elsevier Science Publishers, Amsterdam, vol. 385, No. 3, pp. 171–175.
S. Greiner, et al., "Ectopic Expression of A Tobacco Invertase Inhibitor Homolog Prevents Cold–Induced Sweetening of Potato Tubers", *Nature Biotechnology*, vol. 17, Jul. 1999, pp. 708–711.
H. Weber, et al., "Sugar Import and Metabolism During Seed Development", *Trends in Plant Science*, May 1997, vol. 2, No. 5, pp. 169–174.

* cited by examiner

*Primary Examiner*—David T. Fox
*Assistant Examiner*—Russell Kallis
(74) *Attorney, Agent, or Firm*—Ostrolenk, Farber, Gerb & Soffen, LLP

(57) ABSTRACT

The invention relates to transgenic plants and plant cells comprising a reduced expression of invertase inhibitors. The modification of the expression of the invertase inhibitors is achieved by introducing a cDNA sequence in an antisense orientation with respect to a promoter. The expression of the antisense DNA sequence is under the regulation of either the CaMV35S promoter or a tissue specific promoter.

13 Claims, 5 Drawing Sheets

TRANSGENIC PLANTS AND PLANT CELLS COMPRISING A REDUCED EXPRESSION OF INVERTASE INHIBITORS

This application is a 371 of PCT/EP99/05890 filed Aug. 11, 1999.

FIELD OF THE INVENTION

This invention concerns transgenic plant cells and plants, a method for their preparation and the use of invertase inhibitor cDNA sequences in an antisense or sense orientation to produce such plants.

Improvement in the quality and quantity of plant reserve material in seeds of dicotyledonous and monocotyledonous agriculturally-useful plants represents an important objective of biotechnology research. Hitherto, strategies generally were developed which were based on the introduction of particular genes whose genetic products constituted enzymes which are themselves involved in the synthesis of the energy reserves (e.g. ADP glucosepyrophosphorylase). Furthermore, methods are also described, in which an increased rate of glycolysis is obtained by modified expression of heterologous, and therefore, deregulated invertases or glucokinases in the cytosol (DE-A1-195 29 696). In later variants the increased breakdown of sucrose by a deregulated fungal invertase, in combination with a deregulated bacterial glucokinase, leads to an increased rate of glycolysis. This approach rests on the assumption that the synthesis of stored oils in seeds is stimulated because of the increased concentrations of the intermediates of glycolysis, since the metabolisation of the primary photoassimilate, sucrose, is required for phosphorylised hexoses or the fatty acid precursors, pyruvate and acetyl coenzyme A.

DE-A1-195 29 696 correspondingly describes the introduction of a foreign, e.g. fungal gene for the expression of the invertase. Because of the supply of the foreign gene, this fungal invertase enzyme (which is foreign and therefore is not subjected to any regulation) is formed in an amplified manner by regulating a suitable promoter, by means of which the decomposition of the sucrose catalysed by the invertase into glucose and fructose occurs faster. The resulting production of glucose at a higher rate is to bring about in the end an accelerated production of plant reserve material. This process is based on an intervention in the metabolism in the cell of the seed storage tissue, whereby the assimilate transfer between maternal and seed parenchyma is affected only indirectly.

The importance of cell wall invertase for the development of seeds high in starch and protein is well-known. Thus for example the starch accumulation in corn seed is adversely affected with reduced expression of a cell wall invertase by interference in the assimilate transfer between pedicel and endosperm. Flower-specific cell wall invertase isoforms for different plant species are well-known. For *Nicotiana tabacum*, it was able to be shown that an apoplastic invertase inhibitor is powerfully expressed, particularly in the ovary and stamens. Greiner et al. (Plant Physiol. (1998), 733–742) disclosed the amino acid sequence and cDNA sequence of the mentioned invertase inhibitor as well as its in vitro demonstration of function by means of a heterologous expressed inhibitor protein. However, in vivo inhibition was still not indicated. Moreover, it is well-known that varying isoforms of cell wall invertases and invertase inhibitors exist in different tissues and at different times in plant development.

A specific classification of the activities and their possible combined effects of these two time-specific and tissue-specific occurring proteins has not been feasible until now. There are no known studies of an in vivo situation with regard to the regulation of cell wall invertases by invertase inhibitors. Just as little known, was if and when which isoforms of the cell wall invertases are subjected to endogenous regulation by invertase inhibitors during the seed development and if so, which isoforms of the invertase inhibitors. That is why the specific use of these proteins for the production of beneficial plants has not been possible hitherto.

The technical problem of the invention therefore is to provide transgenic plant cells, plants and a method of producing these, in which the plants are characterised by the production of seeds which, compared to seeds of untransformed plants, have a greater amount of plant reserve material such as carbohydrates, fats or proteins, without endogenous or exogenous proteins being over-expressed and without the phenotype of the plant and its development being impaired.

SUMMARY OF THE INVENTION

The technical problem underlying this invention is provided by a process for producing a transgenic plant with a deregulated invertase activity which stimulates plant development, whereby the process provides for: a nucleotide sequence of an invertase inhibitor to be produced from a cDNA bank of a cell suspension culture or from flowers with young ovules from a plant, or to be derived therefrom; a plant cell of a plant of the same type or variety with a DNA construct, containing the functional nucleotide sequence of an invertase inhibitor bound to at least one regulatory unit to be transformed, cultivated and regenerated to a plant whose seed produces a greater amount of reserve material such as carbohydrates, fat or protein in comparison with plants not transformed with such a DNA construct.

The invention provides in particular for the production of transgenic plants with a modified expression of an invertase inhibitor, preferably an apoplastic invertase inhibitor, whereby the plants are characterised by the expression of invertase inhibitor proteins being reduced or completely eliminated during seed development. The process can be applied advantageously to the most widely different dicotyledonous or monocotyledonous useful plants, for example: rape, sunflower, peanut, oil palm, soy bean, *Calendula officinalis, Coriandrum sativum, Crambe abyssinica,* Cuphea ssp., *Dimorphotheca pluvialis, Euphorbia lagascae, Euphorbia lathyris, Lesquerella grandiflora, Limnanthes alba, Linum usitatissimum, Lunaia annua, Lunara biennis,* Oenothera ssp., *Ricinus communis,* and *Simmondsia chinensis* as plants with seeds storing fat; corn, rice, wheat, barley, oats, and rye as plants with seeds storing starch; and soy bean or pea, for instance, as plants with seeds storing protein.

DETAILED DESCRIPTION OF THE INVENTION

Figure 1:
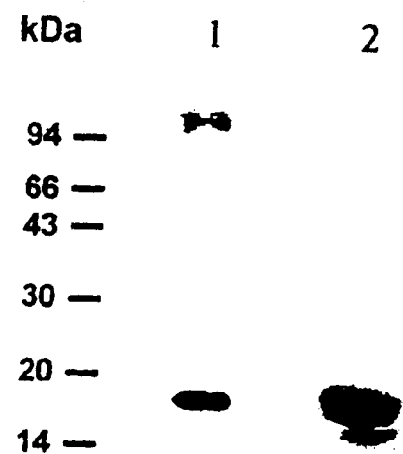
FIG. 1 shows the detection of invertase inhibitors in plants other than tobacco.

Accordingly the invention provides for the transformation of a plant cell with a nucleotide sequence of an invertase inhibitor gene controlled by at least one regulatory unit, the nucleotide sequence of the invertase inhibitor gene being capable of eliminating or reducing the activity of a cell-specific endogenous invertase inhibitor. In a preferred form of implementation, elimination of the activity of an endogenous invertase inhibitor in the cell can be achieved, in that the nucleotide sequence of an invertase inhibitor is inserted in an antisense DNA construct, ie. a construct in which a nucleotide sequence of the invertase inhibitor gene is in an antisense orientation with respect to a promoter. Through the expression, ie. in this context the transcription of the antisense construct, the activity of the cell-specific invertase inhibitor gene is blocked or reduced so that the invertase deregulated in this way leads to an increased accumulation of reserve material in the seed.

In the context of this invention, an antisense construct is understood to mean a DNA construct which has a nucleotide sequence of an invertase inhibitor functionally bound in an antisense orientation to a promoter, this nucleotide sequence being either the full-length cDNA of the invertase inhibitor, a derived sequence thereof or a fragment, an allelic variant or derivative thereof.

In the context of this invention, a sequence derived from a cDNA is understood to mean a man-made or natural nucleotide sequence hybridising with this cDNA sequence, and therefore a nucleotide sequence hybridised with the cDNA sequence of the invertase inhibitor under the conditions described in Sambrook et al. (Molecular Cloning, a laboratory manual, $2^{nd}$ edition (1989), Cold Spring Harbor Laboratory Press), preferably under stringent conditions. According to the invention, hybridising sequences have a sequence identity of 60, 70, 80, 90, 95 or 97%, especially preferred 99%, of the cDNA sequence of an invertase inhibitor gene. Provided that fragments of a cDNA sequence of an invertase inhibitor are used according to the invention, the fragments have at least a length and sequence similarity, which is sufficient, due to hybridisation of a wild-type transcript, to inhibit the translation of an endogenously produced invertase inhibitor mRNA, for example a length of a few hundred base pairs. Obviously provision can also be made for the antisense constructs to have nucleotide sequences of an invertase inhibitor gene or to consist of those which are transcribed but not translated, ie. untranslated regions, or so-called UTR's.

In the context of this invention, DNA constructs, which can cause the elimination or reduction of the activity of an endogenous invertase inhibitor gene, are understood to also mean DNA constructs which have a nucleotide sequence of an invertase inhibitor as defined above or a sequence derived therefrom, which are functionally bound in a sense orientation to at least one regulatory unit, e.g. a promoter. With constructs of this type, the production of endogenous invertase inhibitors can be prevented by co-suppression, for example by a plurality of sense copies of the nucleotide sequence of an invertase inhibitor being available in the genome of the transformed cell and eliminating the expression of endogenous invertase inhibitors.

The constructs according to the invention are preferably arranged in a vector, e.g. in a plasmid, virus, cosmid, bacteriophage or one other standard vector in gene technology.

Provision can be made according to the invention to not only functionally bind the nucleotide sequence of an invertase inhibitor, which is to be used, to a 5'-wards located promoter, but advantageously also to insert a transcription termination signal e.g. from the NOS gene of *Agrobacterium tumefaciens* 3'-wards of the nucleotide sequence. Obviously it also possible to provide additional functional units in the vector, such as T-DNA border sequences or elements stabilising the vectors.

The invention in a preferred way therefore provides plants which have in their seeds an increased amount of reserve material in comparison with untransformed plants, whereby an amount of reserve material increased in comparison means that the average amount of reserve material studied in seeds of a totality of transformed plants is greater than the average amount of the reserve material in question in the seeds of a totality of untransformed plants by predominantly 5, preferably 10, 20, 30, 40, 50, especially preferred 90, 100, 200 or 300%.

The invention therefore concerns the surprising science that, by means of a nucleotide sequence of an invertase inhibitor gene, in particular a cDNA of an invertase inhibitor gene, plants can be produced which in vivo have an increased accumulation of reserve material in the seed, without modifying or impairing the development of the plant in other respects. As well, the invention is based inter alia on the surprising fact that the endogenous invertases are subject to an endogenous regulation by invertase inhibitors during the seed development.

The invention therefore also concerns the use of a nucleotide sequence of an invertase inhibitor gene functionally bound to at least one regulatory unit for the transformation and production of plants which have a modified seed development, and in particular which produce seeds which have an increased amount of reserve material compared to seeds of untransformed plants.

The invention particularly concerns the afore-mentioned use of a nucleotide sequence of an invertase inhibitor gene, this having been obtained from a cDNA bank of a cell suspension culture or from flowers with young ovules of the plant type or if necessary of the plant variety, or having been derived therefrom, which is to be transformed according to the invention with the DNA construct of this invention produced by means of this nucleotide sequence. The nucleotide sequence used for the transformation is consequently the nucleotide sequence or is derived therefrom, which encodes for the predominant isoform of the invertase inhibitor in the cell suspension culture or in the flowers with young ovules.

In the context of this invention, flowers with young ovules are flowers with immature ovules, that is after pollination but before the start of dormancy.

The solution to the technical problem according to the invention is also a transgenic plant cell in which, in comparison with untransformed plant cells, an increased activity of the cell wall invertase is present because of reduced expression of invertase inhibitors, in which transgenic plant cell this reduced expression is produced in an antisense orientation by introducing an invertase inhibitor cDNA corresponding (homologous) to the same plant type and by regulating a promoter. According to the invention, a process for obtaining invertase inhibitor cDNA sequences in a sense orientation or antisense orientation is also provided, the process containing-independently of the respective species-the following steps:

a) producing an inhibitor protein fraction from the cell wall protein fraction of an appropriate cell suspension culture b) production of corresponding peptide sequences after separation and purification of the peptide formed
c) cloning firstly partial cDNA and subsequently full-length cDNA for the invertase inhibitor protein from a cDNA bank
d) cloning of the invertase inhibitor cDNA in a sense orientation or antisense orientation in a vector, e.g. a binary vector
e) transformation of the plant species with the sense orientation or antisense construct.

The assimilate transfer between maternal tissue and seed tissue is the rate-determining step in the production of plant reserve material in seeds. If this step is accelerated by increasing the activity of the cell wall invertase expressed in the transfer zone, the result is an increased accumulation of the principal reserve material of the respective plant type (starch, fat, protein) as a result of the increased assimilate transfer (the increased activity of the cell wall invertase causes an increase in the assimilate transfer between maternal and seed tissue).

The invention also concerns a process for producing the afore-mentioned plants, whereby in a first step an inhibitor protein fraction, in particular the predominant inhibitor protein fraction, from a cell wall protein fraction is obtained from a cell suspension culture or from flowers with young ovules; then in a second step the inhibitor protein fraction is purified, if necessary separated, and at least N-terminal is sequenced, so that a nucleotide can be derived from the amino acid sequence thus obtained; within the framework of a third step by means of for example primers, partial or full-length cDNA for the invertase inhibitor protein is cloned from a cDNA bank of a cell suspension culture or from flowers with young ovules of the same plant or variety mentioned above, then in a fourth step the cDNA obtained is cloned in a vector in a sense orientation or antisense orientation, in order to subsequently transform in a fifth step a plant cell of the same type or variety with the DNA construct thus obtained, this being the type or variety from which the cDNA and the amino acid sequence for the cDNA isolation was obtained.

From that, the invention also concerns plants, and plant components such as root, stem, leaves, cropping and propagating material such as fruit, pollen, seeds, husk, embryo, seedlings, cell cultures, callus tissues etc., produced in accordance with this process. The invention concerns as well any variety or type of plant, and accordingly has no specificity with regard to variety or type whatsoever. The process according to the invention represents an essentially technical process, whereby within its framework a specific allocation of starting material for the means to be used, such as cDNA sequences, is given to a plant ie. the target, which is to be transformed.

Unlike all previous methods, the invention described here is based therefore on the regulation of specific cell wall invertase isoforms expressed during the seed development. The invertase inhibitor cDNA in a preferred form of implementation encodes for an apoplastic variant of the invertase inhibitor. By introducing a single autologous cDNA sequence of plant origin, ie. a cDNA sequence stemming from the organism to be transformed or derived therefrom, the decisive step in the separation of sucrose for the assimilate transfer is modulated at the natural location of activity. The observation that the introduction of at least one sequence, that is of one invertase inhibitor cDNA, in a sense orientation or antisense orientation by controlling, for example, the constitutive CaMV35S promoter, the ubiquitin promoter or zein promoter from corn or a promoter of similarly high or greater activity, e.g. a tissue-specific promoter as well which does not affect entire vegetative plant development, but results in a specific deregulation only during the seed development, shows the extremely high specificity of the transgenic intervention. The advantages of this direct deregulation are obvious: 1) one single gene construct is sufficient to achieve a significant modification of reserve material accumulation; 2) no foreign gene products are produced; 3) the intervention in the metabolism is extremely specific; 4) for tobacco, it is shown by example that the modified expression of an apoplastic invertase inhibitor leads to drastic changes in the production of stored oil.

The modulation, particularly the increase in the accumulation of the seed reserve materials, by a specific modification of the expression of the invertase inhibitor, especially reduction, is based inter alia on the following mechanisms:

a) by modifying the activity phase of the cell wall invertase in the maternal tissue, the efficiency of the nutrient load is affected, ie. is increased for example in inhibitor antisense transforms.

b) The oxidative pentose phosphate cycle is of crucial significance for the synthesis of reserve oils of the seeds. The sustained increased availability of glucose in, for example, inhibitor antisense transforms therefore promotes the synthesis of stored oil.

c) by modifying the ratio of hexoses to sucrose, the cell division phase of the seed development is affected. By extending the activity phase of the cell wall invertase in, for example, inhibitor antisense transforms, the cell count per seed, for instance, is increased.

In comparison with the equally possible overexpression of the cell wall invertase(s) involved in the assimilate transfer, the approach of turning off the invertase inhibitors described here indirectly has even further advantages. The cell wall invertases expressed during seed production are heavily expressed naturally, the scope of additional induction by using strong promoters is limited by this, whereas a large increase in the activity of the cell wall invertase(s) can be obtained by the antisense switching off according to the invention of the inhibitor. In fact, by expressing a heterologous, deregulated, inhibitor-sensitive invertase with a signal peptide for the target control in the cell wall space, a similar effect could be achieved, but in this case foreign proteins have to be used. In addition, with a combination of the seed-specific promoters with a deregulated invertase used for this approach, there is a high risk that too great an expression results in undesired side effects. In contrast to this, in the process described here, the maximum activity of the naturally-occurring cell wall invertases is never exceeded, merely the time span of its activity is prolonged during the accumulation of reserve material. For these reasons, in each case of introducing a heterologous invertase, indirect regulation of the cell wall invertases is to be preferred over antisense expression of invertase inhibitors or, in the framework of the co-suppression technology, over sense DNA constructs and represents a significant technical improvement.

Methods for Obtaining a Homogenous Inhibitor Protein Fraction from the Apoplastic Cell Wall Protein Fraction of a Cell Suspension Culture A cell suspension culture is started from the respective plant species. The process for obtaining a cell culture follows standard protocols of plant tissue culture. As a rule, the cells are started as a shaking culture under sterile conditions in a complex nutrient medium with the addition of sucrose (carbon source). Under these cultivation conditions, plant cells express a cell wall invertase which is regulated by a likewise expressed invertase inhibitor.

The accumulation and purification of the invertase inhibitor is based on its binding to the cell wall invertase. First a cell wall protein fraction is extracted through incubation in 1M NaCl, 1 mM PMSF at 4° C. while shaking. Usually no cytosolic proteins are extracted doing this. The cell wall protein fraction obtained in this way is concentrated through ammonium sulfate precipitation (80%) or through membrane filtration. By means of subsequent chromatography in a concanavalin A column, a glycoprotein fraction is obtained which contains the glycosylated cell wall invertase and the invertase inhibitor bound to this. SDS-PAGE/Western blot analyses of the cell wall invertase fractions, and therefore invertase inhibitor-enriched fractions, obtained in this way with a polyclonal antiserum against the invertase inhibitor from tobacco cells, indicate the presence of invertase inhibitors, generally proteins of 15–25 kDa.

FIG. 1 shows the detection of invertase inhibitors of other plant types which are homologous to the tobacco invertase inhibitor-a Western blot analysis of cell wall protein samples obtained from suspension cultures of *Chenopodium rubrum* (1) and *Daucus carota* (2). The development was carried out with an antiserum produced against the recombinant tobacco invertase inhibitor. Invertase inhibitor polypeptides of approx. 17 kDa were detected for both species.

Further purification of the complexes consisting of cell wall invertase and invertase inhibitor is carried out through ion-exchange chromatography in a cation-exchanger, e.g. sulfopropylsephadex. After sequential chromatography, first of all via a pH gradient (pH8–12), after that via an NaCl gradient, a highly enriched preparation of the cell wall invertase is obtained in which the invertase inhibitor is present with the latter in the stable complex. The peak fractions of the final ion exchange purification are detected through SDS-PAGE/Western blot analysis because of cell wall invertase e.g. with an antiserum against the carrot cell wall invertases. Moreover, the invertase activities of all fractions were determined in the coupled enzymatic test with hexokinase/glucose-6-phosphate dehydrogenase. The fractions with the strong cell wall invertase immune signal but low invertase activity contain the generally high-purity inhibitor protein.

Methods for Obtaining Peptide Sequences of the Purified Invertase Inhibitors

After the purification protocol described above, the inhibitor protein is sufficiently pure to become N-terminal unsequenced after electroblotting directly onto a PMDF membrane. After obtaining 100–500 µg of inhibitor protein, this can if necessary be purified again via SDS-PAGE and then can be digested by trypsin directly in the gel. The separation of the resulting peptides through reverse phase HLPC and its subsequent sequencing through Edman degradation is in accordance with standard procedures. The combination of N-terminal unsequencing and the sequencing of the peptides preserved during tryptic digestion results in sufficient sequencing information for cloning based on the RT-PCR process Process for Cloning, Firstly, Partial cDNA and Subsequently Full-length cDNA for the Respective Invertase Inhibitor Protein from a cDNA Bank Starting from the preserved peptide sequence information, primer sequences are derived according to the genetic code. Standard algorithms are used for the optimum primer design. In another implementation, primers are designed with highly conservative sequence regions of the already known invertase inhibitor sequences from *Nicotiana tabacum, Lycopersicon esculentum, Arabidopsis thaliana* and *Citrus inshui*.

First a single strand CDNA synthesis is carried out according to standard procedures. For this, complete RNA is extracted in accordance with standard procedures from a cell suspension culture, or, in another implementation, from flowers with young ovules. A partial invertase inhibitor cDNA is then first amplified through RT-PCR. In one implementation, the amplification is cloned into the Bluescript vector. After sequencing and confirming a sequence homologous to the known invertase inhibitors, this partial cDNA is used as a probe for the production of full-length clones. For this, either a cDNA bank from a cell suspension culture, or in another implementation, a cDNA bank from flowers with young ovules, is started in accordance with standard procedures.

Cloning of the Invertase Inhibitor cDNA in a Sense Orientation or an Antisense Orientation in a Vector, for Example a Binary Vector In one form of implementation the invertase inhibitor cDNA cloned for each plant type is cloned in the binary vector BinAR (Bin19 derivative) (Höfgen and Willmitzer, Plant Sci. 66 (1990), 221–230). In one form of implementation, the CaMV35S promoter is used for both for antisense and sense constructs, but if necessary other promoters, for example tissue-specific promoters, also can be used.

Figure 2:
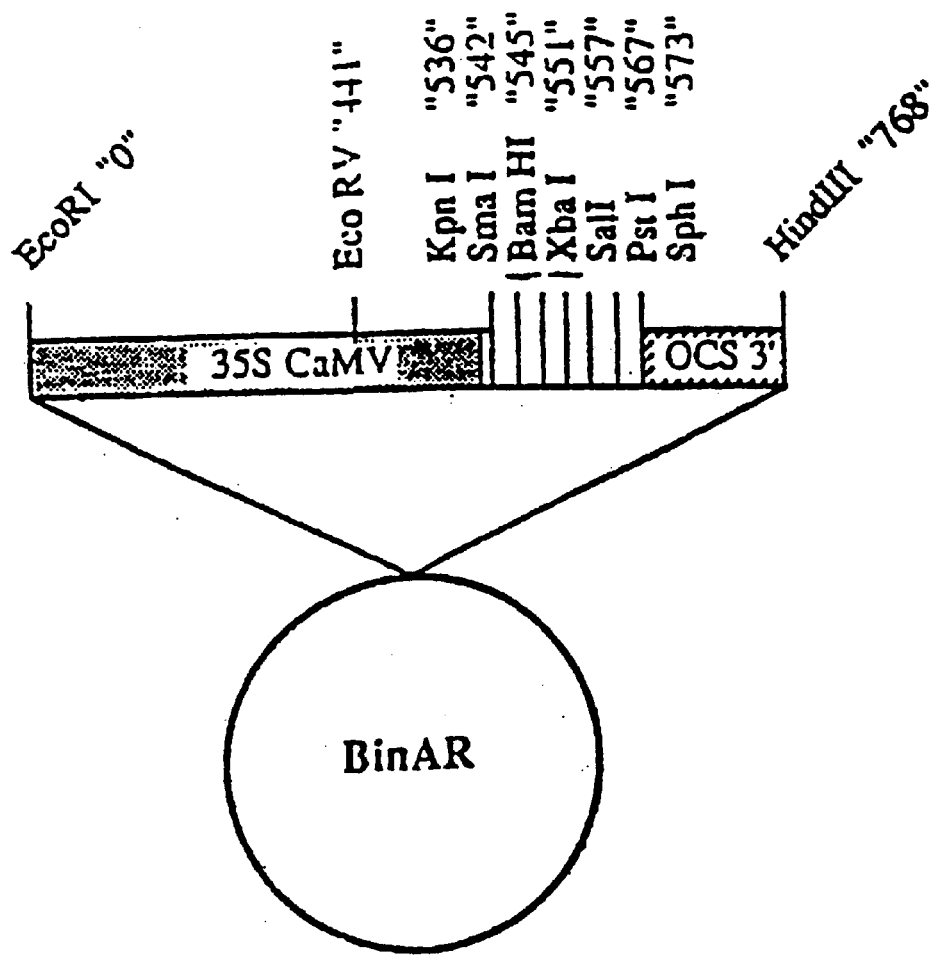
FIG. 2 shows the binary vector (BinAR) for *Agrobacterium tumefaciens*-mediated transformation.

FIG. 2 shows the binary vector (BinAR) for the *Agrobacterium tumefaciens*-mediated transformation. The encoding regions of the invertase inhibitor cDNA are cloned in a sense orientation or antisense orientation in the "multiple cloning site'.

Transformation of the Plant Species with the Sense and Antisense Gene Constructs Respectively For most dicotyledonous useful plants, invertase inhibitor sense/antisense transforms are obtained by using *Agrobacterium tumefaciens*-mediated transformation (standard process). Accordingly an Agrobactedum is used, since it contains recombined DNA molecules which have invertase inhibitor cDNA in antisense orientation or sense orientation, ie. in which the invertase inhibitor cDNA exists 3'-wards from a promoter and functionally bound with the latter. In a form of implementation useable for many plant types, leaf fragments are transformed with this, primary transforms being regenerated from the recombinant cells in an antibiotic-containing medium. The transformation technique actually selected is dependent on the plant type. A transgenic plant is obtained by regeneration of a transformed plant cell.

The influence of the modified expression of an apoplastic invertase inhibitor in *Nicotiana tabacum* is described below:

Tobacco (*Nicotiana tabacum*) was transformed in sense orientation and antisense orientation with the cDNA of the apoplastic tobacco invertase inhibitor (clone Nt-inhl; Greiner et al., loc cit. 1998) (*Agrobacterium tumefaciens*-mediated transformation, BinAR vector, CaMV35S promoter; leaf slice transformation according to standard procedures). The cDNA used was obtained from a cell suspension culture of tobacco. Primary transforms were first regenerated to plants via tissue culture and subsequently brought to flower in the greenhouse. The seeds of the primary transforms were sown on a kanamycin-containing medium. After sterile pre-cultivation the plants of the F1 generation were brought to flower in the greenhouse. After pollination the cell wall invertase activities in the ovaries were determined at regular time intervals.

Figure 3:
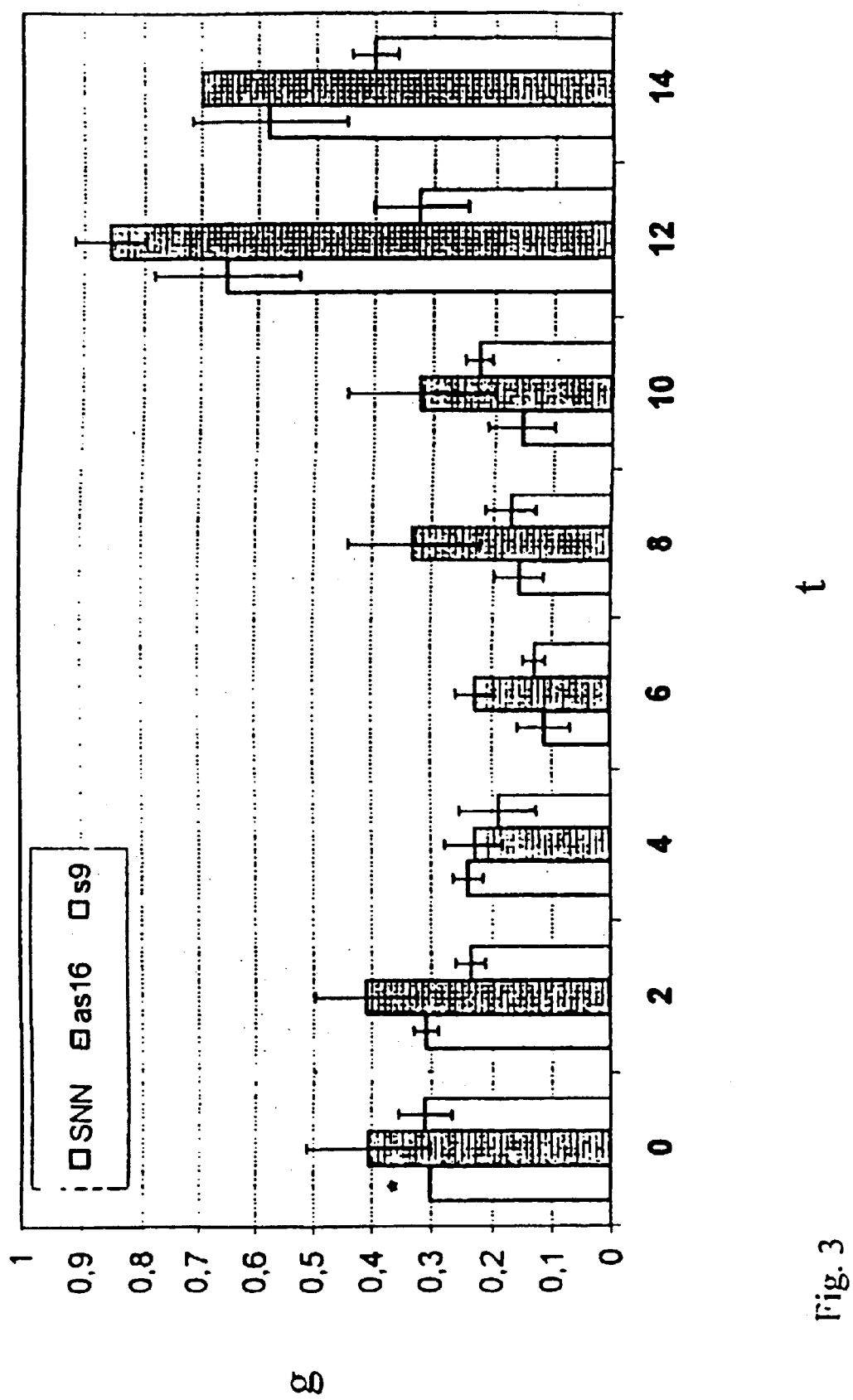
FIG. 3 shows cell wall invertase activities in the ovary of a tobacco wild-type (SNN), an antisense transformant (as16), and a sense transformant (s9).

FIG. 3 shows cell wall invertase activities in the ovary of a tobacco wild-type (SNN), a representative inhibitor antisense transform (as16) and a representative inhibitor sense transform (s9) during the early seed development (0–14 days after fertilisation). The activities are indicated in mmol glucose/g fresh weight/min.

The amount of invertase inhibitor protein was determined through Western blot analysis.

Figure 4:
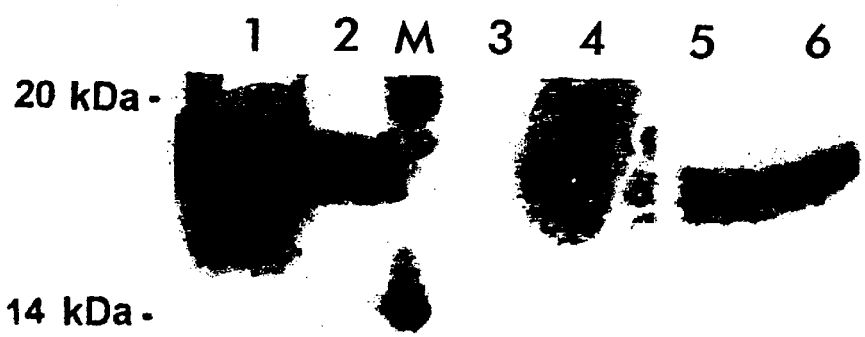
FIG. 4 shows the selective reduction or increase of the invertase inhibitor in stamens and ovaries.

With regard to this, FIG. 4 shows the proof of the selective reduction (antisense transform) or increase (sense transform) of the invertase inhibitor polypeptide in stamens and ovaries, detected with an antisenum directed against the recombinant tobacco invertase inhibitor (sense transform (s9): 1, ovaries; 2, stamens. Antisense transform: 3, ovaries; 4, stamens. Wild-type (SNN): 5, ovaries; 6, stamens). Purified samples, which contain an inhibitor bound only to a cell wall invertase, were plotted through concanavalin A chromatography.

After maturation of the seeds, their dry weights were determined, as well as the amount of stored oil and total protein.

Measurement of the cell wall invertase activities during the early seed development (FIG. 3) shows first of all an approximately 6-fold increase for the wild-type between the $6^{th}$ and $12^{th}$ day after pollination. This period corresponds to the late cell division phase and the beginning of the storage phase. The Western blot analysis shows that in the ovary the amount of invertase inhibitor polypeptide in antisense transforms is sharply decreased, however it is greatly increased in antisense transforms (FIG. 4). In contrast to this, the modified inhibitor expression is obtained only slightly in stamens, presumably because several inhibitor isoforms are expressed in this tissue.

The modified activity of the cell wall invertase during the seed development has an effect on the dry weight/seed (Table 1), the stored oil content/seed (Table 2) and the total protein content/seed (Table 3), but not on the total number of seeds per flower and also not on the seed size.

TABLE 1

Dry weight per seed in tobacco wild-type (SNN), in two representative inhibitor sense transforms (s9, s10) and in two representative inhibitor antisense transforms (as16, as43).

| Tobacco Line | µg Dry Weight/Seed | Percent of Wild-type (SNN) |
|---|---|---|
| WT (SNN) | 64 ± 2 | 100 |
| s9 | 42 ± 2 | 66 |
| s10 | 52 ± 2 | 81 |
| as16 | 71 ± 1 | 110 |
| as43 | 86 ± 4 | 134 |

TABLE 2

Seed oil content per seed in tobacco wild-type (SNN), in two representative inhibitor sense transforms (s9, s10) and in two representative inhibitor antisense transforms (as16, as43).

| Tobacco Line | µg Total Oil/Seed | Percent of Wild-type (SNN) |
|---|---|---|
| WT (SNN) | 23 | 100 |
| s9 | 10 | 43 |
| s10 | 16 | 69 |
| as16 | 28 | 122 |
| as43 | 39 | 170 |

TABLE 3

Total protein per seed in tobacco wild-type (SNN), in two representative inhibitor sense transforms (s9, s10) and in two representative inhibitor antisense transforms (as16, as43).

| Tobacco Line | µg Total Protein/Seed | Percent of Wild-type (SNN) |
|---|---|---|
| WT (SNN) | 7.4 | 100 |
| s9 | 5.5 | 74 |
| s10 | 5.7 | 77 |
| as16 | 7.8 | 105 |
| as43 | 9.9 | 134 |

The large increase in stored oil content in two individual antisense transforms (+22% and +70% respectively) correlates with increases in total protein and seed weight, the increase for stored oil being most marked. Remarkably the increase in the cell wall invertase activity in the ovary during the seed development corresponds to the phase of the maximum accumulation of stored oil.

The entire vegetative development phase of the inhibitor antisense and inhibitor sense transforms proceeds with no visible phenotype, with the exception of the germination process. Here there is no difference between the germination of tobacco wild-type seeds and invertase inhibitor antisense seeds, whereas with seeds of invertase inhibitor sense transforms there is a significant delay in germination.

Figure 5:
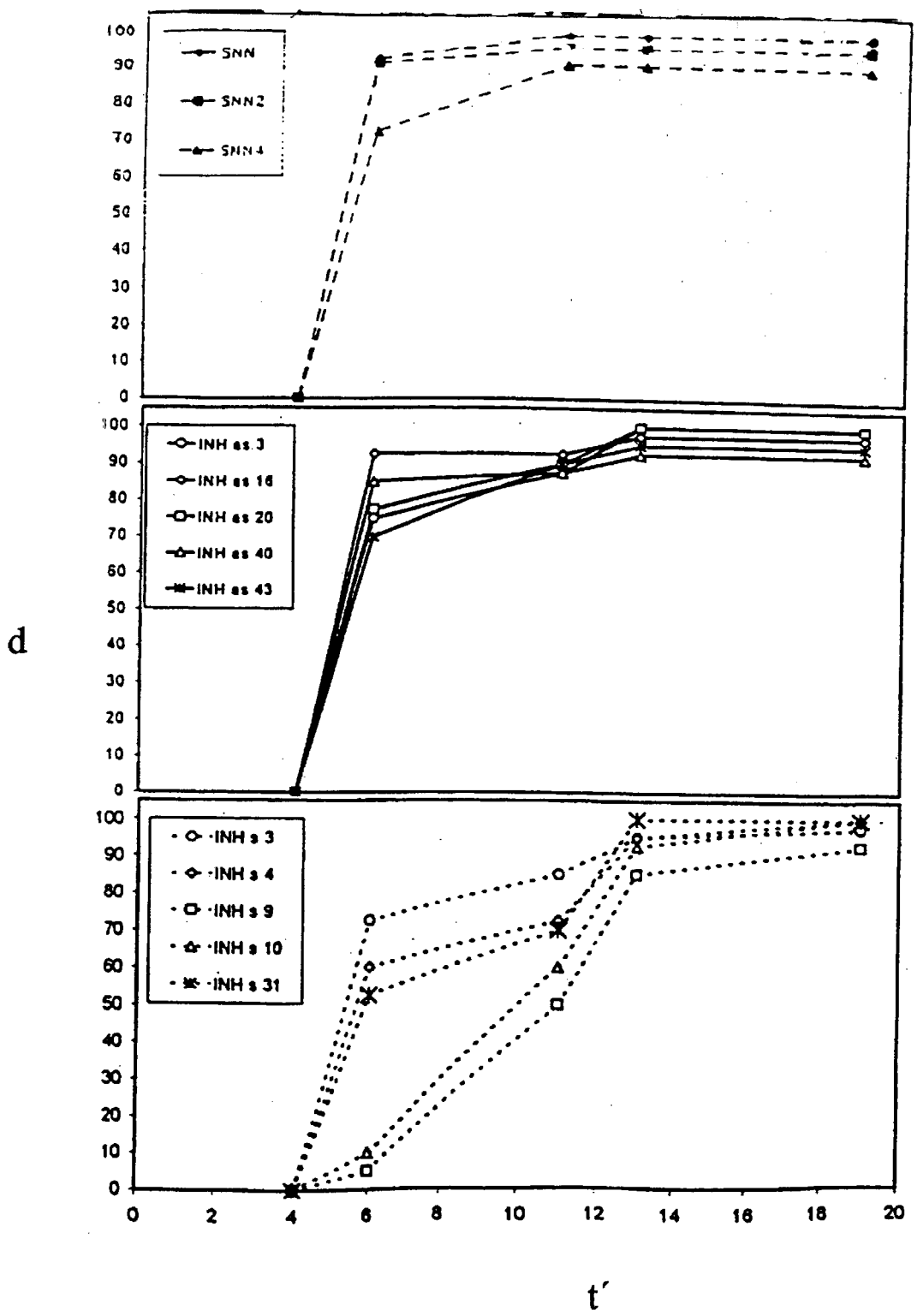
FIG. 5 shows germination of wild-type, antisense transformant, or sense transformant tobacco seeds.

FIG. 5 shows the germination behaviour of seeds of tobacco wild-type (SNN), of invertase inhibitor antisense transforms (INHas) and of invertase inhibitor sense transforms. Per line, in each case 40 seeds were sown on an LS medium (0.5% sucrose, pH5.6) under sterile conditions. The protrusion of the radicle is used as the criterion for germination.

A further example of application of this invention is the introduction of an invertase inhibitor antisense construct in rape (*Brassica napus*). On a seed basis, rape contains an amount of stored oil comparable to tobacco. The result of an invertase inhibitor antisense transformation is an increase in the stored oil content by at least 20%, and possibly by up to 70%.

A further application with the same objective, namely increasing the stored oil content, is the transformation of the sunflower, or perhaps the transformation of the soy bean, with an invertase inhibitor antisense construct (making available transgenic oil-storing plants of these species).

In an additional form of implementation, the amount of seed stored starch is increased by putting invertase inhibitor antisense constructs into corn, rice, wheat, oats, barley and rye. Thus transgenic plant cells or plants, which store starch, can be provided. In a further form of implementation, for protein-rich seeds, e.g. soy bean and pea, the total amount of stored protein is increased by introducing invertase inhibitor antisense constructs.

In an additional implementation form, the germinating capability of seeds of a useful plant is increased by introducing invertase inhibitor antisense constructs, or that is to say, by the enhanced reserve material accumulation resulting therefrom.

The preparation of transgenic plant cells or plants preferably concerns useful plants.

I claim:

1. A process for producing a transgenic plant, whose seeds have an increased amount of reserve material in comparison with a wild-type plant due to the reduction or elimination of the expression of an endogenous invertase inhibitor protein during the development of seeds so that the activity of invertase, which is subject to a regulation by the invertase inhibitor protein, is increased during the development of seeds leading to an increased accumulation of reserve material in the seed, said process comprising the steps of:

(a) obtaining a nucleotide sequence coding for the invertase inhibitor protein expressed during seed development in flowers with young ovules;

(b) inserting the coding nucleotide sequence in a DNA construct in anti-sense orientation next to a promoter as a regulatory unit;

(c) transforming a plant cell of a plant, from which the coding nucleotide sequence was obtained, with the DNA construct; and (d) cultivating the plant cell and regenerating a plant, wherein the expression of the endogenous invertase inhibitor protein is reduced or eliminated during seed development.

2. Process according to claim 1, wherein the nucleotide sequence coding for an invertase inhibitor protein is a cDNA, obtained by the following steps:

(a) separating and purifying an inhibitor protein fraction from the cell wall protein fraction of flowers with young ovules of a plant;

(b) digesting the inhibitor protein and separation of the resulting peptides;

(c) sequencing the peptides in order to obtain the amino acid sequences;

(d) deriving nucleotide sequences from the amino acid sequences and designing of primers; and (e) cloning a partial or full-length cDNA coding the invertase inhibitor protein from a cDNA library from flowers with young ovules of said plant or alternatively synthesizing the partial or full-length cDNA using the primers.

3. A process according to claim 1, in which the promoter is a constitutive or inducible promoter.

4. A process according to claim 3, in which the promoter is selected from the group consisting of CaMV35S promoter, ubiquitin promoter, and zein promoter from corn.

5. A process according to claim 1, in which the invertase inhibitor is an apoplastic invertase inhibitor.

6. A process according to claim 1, in which the DNA construct has additional regulatory units.

7. A process according to claim 6, in which an additional regulatory unit is a transcription termination signal.

8. A process according to claim 7, in which the transcription termination signal comes from a NOS gene of *Agrobacterium tumefaciens*.

9. A process according to claim 1, in which the plant cell is a cell of a dicotyledonous or monocotyledonous plant.

10. A process according to claim 9, in which the plant cell is from a plant selected from the group consisting of rape, sunflower, peanut, soy bean, oil palm, rice, corn, wheat, barley, oats, rye, pea, *Calendula officinalis, Coriandrum sativum, Crambe abyssinica*, Cuphea ssp., *Dimorphotheca pluvialis, Euphorbia lagascae, Euphorbia lathyris, Lesquerella grandiflora, Limnanthes alba, Linum usitatissimum, Lunaria annua, Lunaria biennis*, Oenothera ssp., *Ricinus communis* and *Simmondsia chinensis*.

11. A process according to claim 1, in which the DNA construct is in a vector.

12. A process according to claim 11, in which the vector is a plasmid or a virus.

13. A process according to claim 1, in which the transformation of the plant cell is carried out by an *Agrobacterium tumefaciens*-mediated transformation or a biolytic process comprising a step selected from the group consisting of electrically induced DNA absorption, chemically induced DNA absorption, electroporation, macroinjection, microinjection and PEG-mediated transformation.

* * * * *